(12) United States Patent
Aujla

(10) Patent No.: US 10,758,304 B2
(45) Date of Patent: Sep. 1, 2020

(54) BASKET CATHETER WITH AN IMPROVED SEAL

(71) Applicant: Biosense Webster (Israel) Ltd., Yokneam (IL)

(72) Inventor: Vishav Manak Singh Aujla, Valencia, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 855 days.

(21) Appl. No.: 14/960,777

(22) Filed: Dec. 7, 2015

(65) Prior Publication Data

US 2017/0156790 A1 Jun. 8, 2017

(51) Int. Cl.
| | | |
|---|---|---|
| A61B 18/14 | (2006.01) |
| A61B 5/042 | (2006.01) |
| A61N 1/06 | (2006.01) |
| A61B 5/00 | (2006.01) |

(Continued)

(52) U.S. Cl.
CPC ........ *A61B 18/1492* (2013.01); *A61B 5/0422* (2013.01); *A61B 5/4836* (2013.01); *A61N 1/06* (2013.01); *A61B 5/6843* (2013.01); *A61B 5/6858* (2013.01); *A61B 2018/0016* (2013.01); *A61B 2018/00267* (2013.01); *A61B 2018/00351* (2013.01); *A61B 2018/00577* (2013.01);
(Continued)

(58) Field of Classification Search
CPC ...... A61B 18/1492; A61B 2018/00577; A61B 2018/00351; A61B 2018/00357; A61B 2018/00267; A61B 2018/00214; A61B 2018/00273; A61B 2018/00279; A61B 2018/1407; A61B 2018/144; A61B 2018/0016; A61B 2018/1465; A61B 2018/1467; A61B 2018/1475; A61B 5/6858; A61B 5/0422; A61B 2218/002
USPC ........... 606/41; 607/104, 105, 113, 115, 116, 607/119, 122, 126, 130
See application file for complete search history.

(56) References Cited

U.S. PATENT DOCUMENTS

| | | |
|---|---|---|
| 5,391,199 A | 2/1995 | Ben-Haim |
| 6,064,905 A | 5/2000 | Webster et al. |
| 6,239,724 B1 | 5/2001 | Doron et al. |

(Continued)

FOREIGN PATENT DOCUMENTS

| | | |
|---|---|---|
| EP | 2201905 A1 | 6/2010 |
| WO | 94/07413 A1 | 4/1994 |

(Continued)

OTHER PUBLICATIONS

Notification of Intent to Grant for corresponding European Patent Application No. 16202461.6, dated May 8, 2018.

(Continued)

*Primary Examiner* — Thomas A Giuliani
(74) *Attorney, Agent, or Firm* — Dergosits & Noah LLP; Todd A. Noah

(57) ABSTRACT

Systems and methods are disclosed for providing and using an irrigated ablation catheter. The catheter includes a distal electrode assembly having a plurality of spines forming a basket shaped electrode assembly in communication with a system controller. The catheter also includes a pull-wire disposed within a lumen of a spine collar. The spine collar further includes a silicone seal for preventing encroachment of irrigation fluid and other bodily fluids into the pull-wire lumen.

17 Claims, 6 Drawing Sheets

(51) Int. Cl.
*A61B 18/00* (2006.01)
*A61B 34/20* (2016.01)

(52) U.S. Cl.
CPC .............. *A61B 2018/1467* (2013.01); *A61B 2034/2051* (2016.02); *A61B 2218/002* (2013.01)

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 2002/0065455 A1 | 5/2002 | Ben-Haim |
| 2003/0120150 A1 | 6/2003 | Govari |
| 2004/0068178 A1 | 4/2004 | Govari |
| 2007/0106292 A1* | 5/2007 | Kaplan .............. A61B 18/1492 606/41 |
| 2012/0271138 A1 | 10/2012 | Kordis et al. |

FOREIGN PATENT DOCUMENTS

| | | | |
|---|---|---|---|
| WO | 96/05768 | 9/1996 | |
| WO | 2004/112629 A1 | 12/2004 | |
| WO | WO 2004/112629 A1 * | 12/2004 | ............. A61B 18/18 |

OTHER PUBLICATIONS

European Search Report from corresponding European Patent Application 16202461.6, dated Apr. 5, 2017, 1-7 pages.

* cited by examiner

BASKET CATHETER WITH AN IMPROVED SEAL

FIELD OF THE PRESENT DISCLOSURE

This disclosure relates generally to methods and devices for percutaneous medical treatment, and specifically to catheters, in particular, ablation catheters. More particularly, this disclosure relates to irrigated ablation catheter designs featuring a basket-shaped ablation electrode array having an improved seal.

BACKGROUND

Radiofrequency (RF) electrode catheters have been in common use in medical practice for many years. They are used to stimulate and map electrical activity in the heart and to ablate sites of aberrant electrical activity. Specifically, targeted ablation may be performed for a number of indications. For example, ablation of myocardial tissue is well known as a treatment for cardiac arrhythmias by using a catheter to apply RF energy and create a lesion to break arrhythmogenic current paths in the cardiac tissue. As another example, a renal ablation procedure may involve the insertion of a catheter having an electrode at its distal end into a renal artery in order to complete a circumferential lesion in the artery in order to denervate the artery for the treatment of hypertension.

In many of these procedures, a basket shaped electrode catheter is used. Basket shaped catheters have several spines or arms connected together at both of their proximal and distal ends. In many of these basket shaped catheters, movement of these spines into a basket is done by longitudinal translation of a pull-wire connected to the distal ends of the spines. The pull-wire extends the length of the catheter, from the proximal handle to the multitude of spines. One problem with these arrangements is that the lumen housing the pull-wire is an open lumen, allowing irrigation fluid as well as bodily fluids to move into the lumen. Exposure of the proximal end of the catheter body to fluids may interfere with the wires electrically connecting the electrodes and sensors to the control panel causing a disruption of the procedure. Prior art catheters have attempted to prevent the back-flow of fluids into the pull-wire lumen using an O-ring or liquid sealant, but these have proven unsuccessful.

Accordingly, it would be desirable to provide an irrigated ablation catheter that has an improved sealing arrangement for the pull-wire lumen that overcomes these and other disadvantages. As will be described in the following materials, this disclosure satisfies these and other needs.

SUMMARY

The present disclosure is directed to catheter, comprising an elongated body, an electrode assembly mounted at a distal end of the elongated body; and a first inner and second inner lumen disposed within the elongated body, and a seal having a first opening corresponding to the first inner lumen and a second opening corresponding to the second inner lumen, the seal fixedly attached to a distal end of the elongated body.

In one aspect, the elongated body further comprises a spine collar having a plurality of outer lumens and wherein the first inner lumen and second inner lumen are disposed within the spine collar.

In one aspect, the electrode assembly includes a plurality of spines, the plurality of spines forming a basket-shaped electrode assembly and wherein each of the plurality of spines is attached to and in communication with one of the plurality of outer lumens.

In one aspect, the second inner lumen houses a pull-wire, the pull-wire disposed longitudinally within the second inner lumen and where the second opening of the seal is of a dimension to provide a friction fit seal around an outer surface of the pull-wire.

In one aspect, the seal is composed of silicon where the first opening and the second opening are laser cut.

In one aspect, each spine comprises at least one ring electrode where the at least one ring electrode has at least one wire in electrical communication with a controller.

In one aspect, the catheter also includes at least one sensor operably connected to the electrode assembly and to a controller.

In one aspect, the first inner lumen is an irrigation lumen.

This disclosure is also directed to a method for the ablation of a portion of tissue of a patient by an operator comprising inserting a catheter into the patient, the catheter comprises an elongated body, an electrode assembly mounted at a distal end of the elongated body, a first inner lumen disposed within the elongated body, a second inner lumen disposed adjacent to the first inner lumen, and a seal, the seal having a first opening corresponding to the first inner lumen and a second opening corresponding to the second inner lumen, the seal fixedly attached to a distal end of the elongated body. The method further includes connecting the catheter to a system controller capable of receiving signals from a plurality of sensors and delivering power to the electrode assembly and controlling the power to the electrode assembly to ablate the tissue.

In one aspect, the method includes controlling the power to the electrode to ablate tissue is based at least in part on measurements from the plurality of sensors.

In one aspect, the method also includes inserting an elongated body having a spine collar with a plurality of outer lumens and wherein the first inner lumen and second inner lumen are disposed within the spine collar. Further, the second opening of the seal is of a dimension to provide a friction fit seal around an outer surface of the pull-wire.

In one aspect, the method also includes digitizing signals received from the sensors before transmitting them along the elongated body.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

The invention is directed to a catheter having a basket-shaped electrode array having a distal assembly comprising a plurality of spines. The distal assembly carries at least one position sensor and each spine carries at least one electrode, preferably at least one ring electrode, such that when the spines are positioned in contact with tissue in a tubular region of cardiovascular tissue, each spine is capable of obtaining electrical, mechanical and locational data for mapping and/or transmitting and receiving electrical energy, e.g., RF energy, for ablating.

Figure 1:
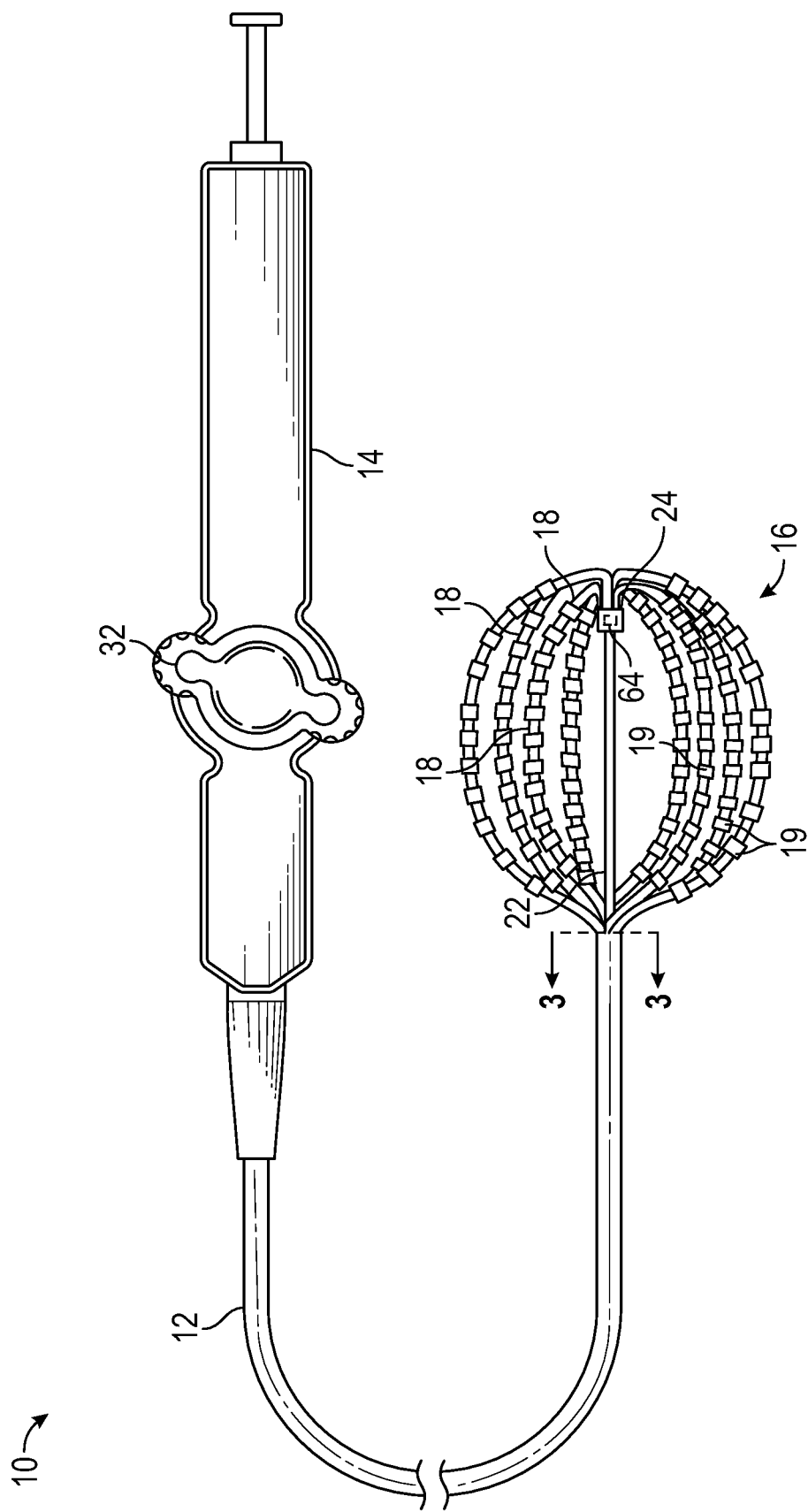
FIG. 1 is a perspective view of a catheter in accordance with an embodiment of the present invention.

As shown in FIG. 1, the catheter 10 comprises an elongated catheter body 12 having proximal and distal ends and a control handle 14 at the proximal end of the catheter body, with a basket-shaped electrode assembly 16 having a plurality of spines 18, each carrying multiple electrodes 19, mounted at the distal end of the catheter body 12. The catheter body 12 comprises an elongated tubular construction having a single, axial or central lumen (not shown), but can optionally have multiple lumens if desired. To enable accurate mapping of electrical signals, for example to detect most or substantially all of the electrical function of the right or left atrium in as little as a single heartbeat, it may be desirable to provide an array of electrodes with a relatively high density. As such, numbers of spines 18 employed may be eight, ten, twelve or any other suitable number. Spines 18 may be evenly or unevenly distributed radially. Further, each spine 18 may include multiple electrodes 19, such as at least ten and up to approximately 16 electrodes per spine. Similarly, the electrodes may be evenly distributed along the spine or may be skewed proximally, centrally or distally to facilitate analysis of the measured electrical signals.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. The outer diameter of the catheter body 12 is not critical, but generally should be as small as possible and may be no more than about 10 french depending on the desired application. Likewise the thickness of the outer wall is not critical, but may be thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

The basket-shaped electrode assembly 16 may also include a puller 22 is generally coaxial with the catheter body 12 and extends from the proximal end of catheter body 12 through the central lumen and is attached, directly or indirectly, to the distal ends of spines 18. The puller 22 is afforded longitudinal movement relative to the catheter body so that it can move the distal ends of the spines 18 proximally or distally relative to the catheter body 12 to radially expand and contract, respectively, the electrode assembly. Since the proximal ends of spines 18 are secured to the catheter body 12, the distance between the distal and proximal ends of spines 18 shortens when they bow outwards into an expanded arrangement, which may be associated with relative movement of puller 22 in the proximal direction. Alternatively or in addition, spines 18 may include a material as described below that facilitates assuming the expanded arrangement, such as a shape memory material, so that puller 22 may be omitted or may be used to aid the transition between the expanded and collapsed arrangements. In an embodiment, the puller 22 may comprise a wire or hypotube formed from a suitable shape memory material, such as a nickel titanium alloy as described below. As will be appreciated, different relative amounts of movement of the puller 22 along the longitudinal axis may affect the degree of bowing, such as to enable the spines 18 to exert greater pressure on the atrial tissue for better contact between the tissue and the electrodes on the spines. Thus, a user can modify the shape of the electrode assembly by adjusting the longitudinal extension or withdrawal of the puller.

A first range of travel of puller 22 from its most distal location to a relatively more proximal location corresponds to deflection of basket-shaped electrode assembly 16 from a collapsed configuration to a first deployed expanded configuration having the generally ellipsoidal shape shown in FIG. 1. When in the collapsed configuration, the spines may be constrained, such as by a guiding sheath. Further, spines 18 may include a sufficient resilient material so that they assume the first expanded deployed configuration when unconstrained with relatively little or no force applied to puller 22. Alternatively, spines 18 may be configured to remain in the collapsed configuration even when unconstrained so that they may be deflected from the collapsed configuration to the first expanded deployed configuration by imparting sufficient force to puller 22. As will be appreciated, in the collapsed configuration, spines 18 assume a generally linear alignment with the catheter body 12 to minimize the outer diameter for insertion within and withdrawal from the patient. In expanding to the first deployed expanded configuration, spines 18 of basket-shaped electrode assembly 16 bow outwards. When positioned at a desired location within a patient, assuming the first deployed expanded configuration may bring electrodes 19 into contract or closer proximity with the walls of the chamber. In one aspect, the ellipsoidal shape of basket-shaped electrode assembly 16 in the first deployed expanded configuration may be characterized as having a length along its longitudinal axis that is at least equal to a length along its equatorial axis. Further, in some embodiments the longitudinal axis length is greater than the equatorial axis length, so that the longitudinal axis length to the equatorial axis length may have a ratio in the range of 5-9:5-8, such as the ratios of 5.5:5, 6.5:6 and 7:6 which are exemplary only and not limiting. In one embodiment, basket-shaped electrode assembly 16 may have a length of approximately 65 mm and a width of approximately 55 mm when in the first deployed expanded configuration. Different ratios and sizes may be employed depending on the patient's anatomy to provide a close fit to the area of the patient being investigated, such as the right or left atria.

Figure 2:
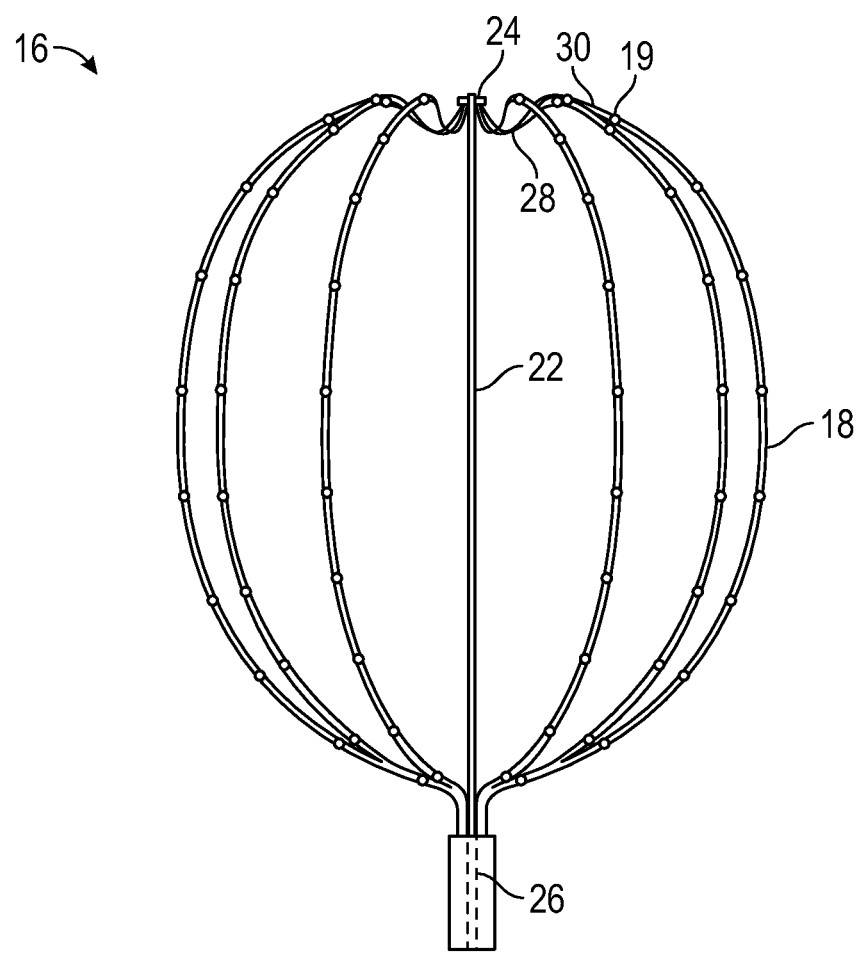
FIG. 2 is a perspective view of a distal electrode assembly of the catheter of FIG. 1 in accordance with an embodiment of the present invention.

A detailed view of one embodiment of the basket-shaped electrode assembly 16 is shown in FIG. 2, showing six spines 18, each carrying ten electrodes 19, of a ten total spine configuration (the middle four spines are omitted in this view to improve clarity). As noted above, in other embodiments, different numbers of spines 18 and/or electrodes 20 may be employed, each of which may be evenly or unevenly distributed as desired. The distal ends of the spines 18 and the puller 22 may be secured to a distal cap 24. Correspondingly, the proximal ends of the spines 18 may be secured to the distal end of the catheter body 12, while the puller 22 may be routed through lumen 26 of the catheter body 12 so that the proximal end extends to the control handle 14. In some embodiments, lumen 26 may also be used to supply a suitable irrigation fluid, such as heparinized saline, to the basket-shaped electrode assembly 16. A fitting (not shown) in the control handle 14 may be provided to conduct irrigation fluid from a suitable source or pump into the lumen 26.

Each spine 18 may comprise a flexible wire 28 with a non-conductive covering 30 on which one or more of the ring electrodes 19 are mounted. In an embodiment, the flexible wires 28 may be formed from a shape memory material to facilitate the transition between expanded and collapsed arrangements and the non-conductive coverings 30 may each comprise a biocompatible plastic tubing, such as polyurethane or polyimide tubing. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, the basket-shaped electrode assembly 16 may have a three dimensional shape that can be easily collapsed to be fed into a guiding sheath and then readily returned to its expanded shape memory configuration upon delivery to the desired region of the patient upon removal of the guiding sheath.

Alternatively, in some embodiments the spines 18 can be designed without the internal flexible wire 28 if a sufficiently rigid nonconductive material is used for the non-conductive covering 30 to permit radial expansion of the basket-shaped electrode assembly 16, so long as the spine has an outer surface that is non-conductive over at least a part of its surface for mounting of the ring electrodes 19.

In some embodiments, puller 22 may be coupled to an actuator 32 on control handle 14 as shown in FIG. 1. Actuator 32 may be a sliding lever, a rotating knob or any other suitable implementation. As such, actuator 32 may be used to adjust the relative longitudinal position of puller 22 and in particular may be configured to adjust the position of puller 22 at least through the second range of travel. Further, actuator 32 may be configured to hold puller 22 in an adjusted position that corresponds to a desired configuration of ellipsoidal basket-shaped electrode assembly 16, such as the first deployed expanded configuration and/or the second deployed expanded configuration as well as intermediate positions if desired.

Figure 3:
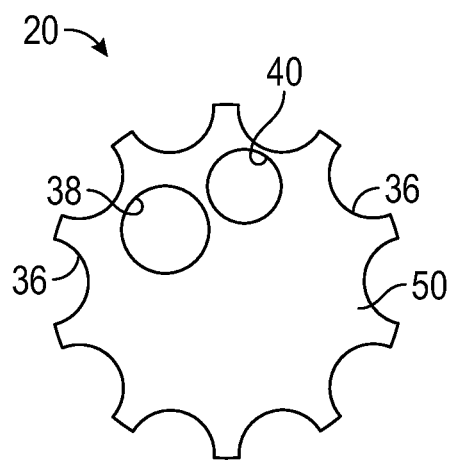
FIG. 3 is a cross section of the distal end of a spine collar in accordance with an embodiment of the present invention.

Referring now to FIG. 3 to FIG. 6, catheter body 12 further comprises a spine collar 20. FIG. 3 illustrates a cross section of spine collar 20. In one embodiment, spine collar 20 is composed of stainless steel. In another embodiment, spine collar 20 is composed of PEEK or other suitable polymer. Spine collar 20 has a length that spans the distance from the handle 16 to proximate the distal end of catheter body 12. Spine collar 20 includes a plurality of longitudinal outer lumens 36. Each of the outer lumens 36 is disposed equidistantly about an outer perimeter of spine collar 20. The number of outer lumens 36 may correspond to the number of spines 18 of the basket-shaped electrode assembly 16. In one embodiment, spine collar 20 has ten longitudinal outer lumens 36 corresponding to ten electrode spines 18. In another embodiment, the number of longitudinal outer lumens 36 and corresponding electrode spines 18 may range from at least 6 to 18 depending on the application of the catheter. Outer lumens 36 house the necessary wires that extend from the electrodes and sensors of distal assembly 16, through handle 14 to operably connect the electrodes and sensors to the controller. In one embodiment, each of the outer lumen 36 is filled with an epoxy resin to protect and keep the wires in place during storage and use of the catheter.

Spine collar 20 further includes at least two inner lumens 38 and 40. Inner lumens 38 and 40 are radially spaced from the center of catheter body 12. In one embodiment, the diameter of inner lumen 38 is slightly larger than the diameter of inner lumen 40. In another embodiment, the diameters are substantially equal in size. In one embodiment, inner lumen 38 is an irrigation lumen. Irrigation lumen 38 may also include a polymer sheath to line the stainless steel lumen. In one embodiment, this polymer sheath comprises Polyimide or any other biocompatible material, as is known in the art. Irrigation lumen 38 has a length that stretches from the handle 14 to the distal end of catheter body 12. Irrigation lumen 38 is in fluid communication with an external source of irrigation fluid for use during the procedure.

Inner lumen 40 comprises a pull-wire lumen for housing the pull-wire 22. Pull-wire lumen 40 has a length that is similar to the length of irrigation lumen 38. In one embodiment, pull-wire lumen 40 includes a plastic sheath to house pull-wire 22. In one embodiment, the plastic sheath comprises a polyether ether ketone (PEEK) or other polymer material. In another embodiment, pull-wire lumen 40 includes a lubricious coating such as polytetrafluoroethylene (PTFE) to facilitate the longitudinal translation of pull-wire 22.

Figure 4:
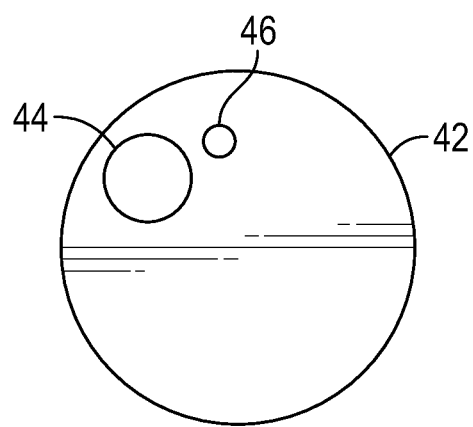
FIG. 4 is a cross section of a seal in accordance with an embodiment of the present invention.
Figure 5:
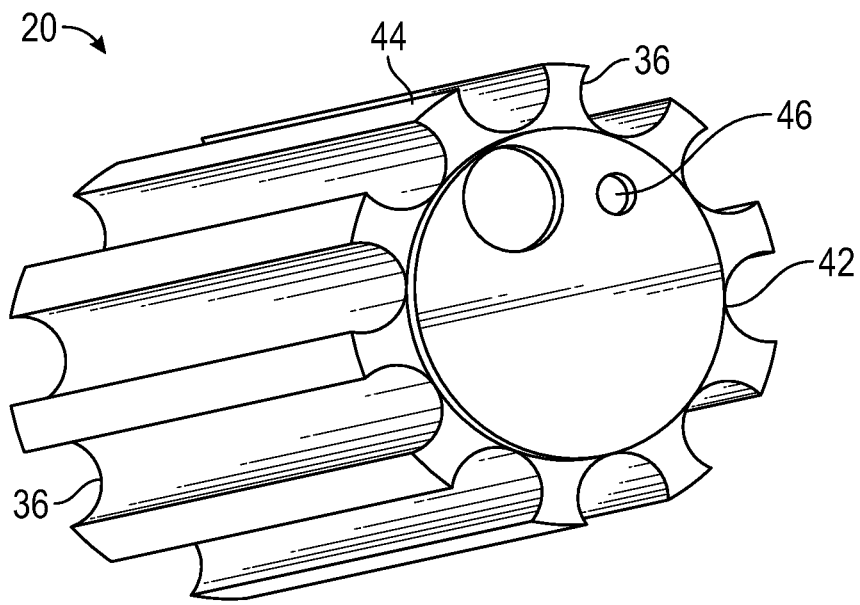
FIG. 5 is a perspective view of a spine collar with seal in accordance with an embodiment of the present invention.
Figure 6:
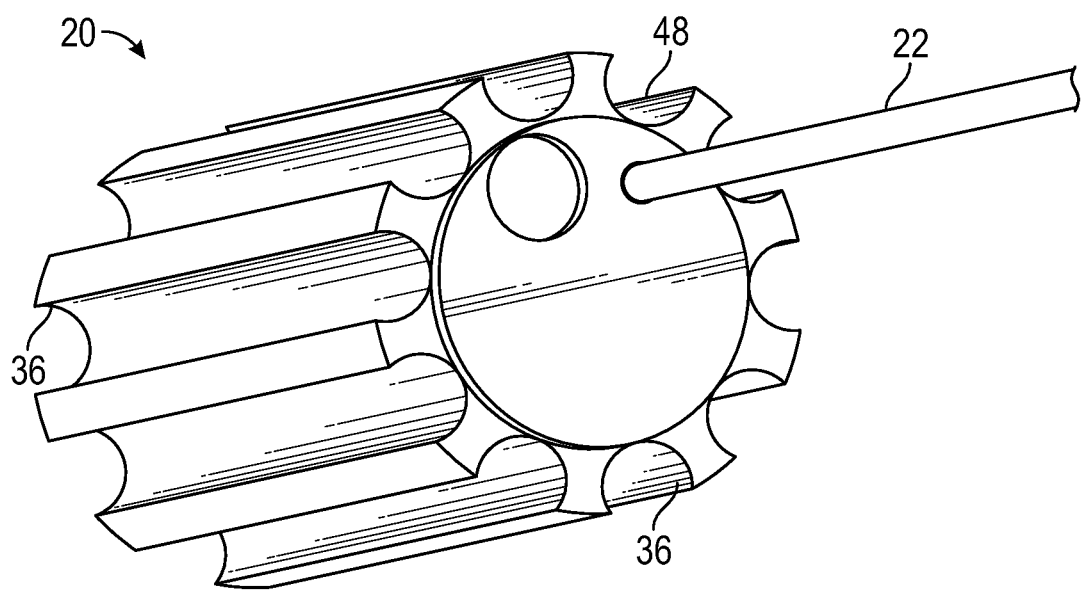
FIG. 6 is a perspective view of a spines collar and seal with a pull-wire in accordance with an embodiment of the present invention.

Turning now to FIGS. 4 and 5, illustrated is an inventive seal 42. Seal 42 comprises a silicone disk having two openings 44 and 46, each of which correspond to inner lumens 38 and 40, respectively. In one embodiment, openings 44 and 46 are laser cut into a sheet of silicon. In a preferred embodiment, the silicon sheet has a thickness of 2 mm. In other embodiments, the silicon sheet has a thickness between 0.5 mm and 4 mm. Opening 44 has a diameter that is substantially equal to the diameter of irrigation lumen 38 to allow for the free flow of irrigation fluid from irrigation lumen 38 to the treatment site.

Opening 46 comprises a pull-wire seal 48, for preventing bodily fluids or other liquids from entering pull-wire lumen 40 during use. As shown in FIG. 4, opening 46 has a diameter that is substantially smaller then the diameter of pull-wire lumen 40, as shown in FIG. 3. Pull-wire seal 48 has a dimension that creates a friction fit around pull-wire 22. Pull-wire seal 48 allows for the translation of pull-wire 22 while at the same time providing a seal to prevent fluid encroachment within the pull-wire lumen. Seal 42 is fixedly attached to the distal end surface 50 of spine collar 20 using, in one embodiment, a polyurethane epoxy. In other embodiments, other biocompatible adhesives may be used to adhere seal 42 to spine collar 20.

Figure 7:
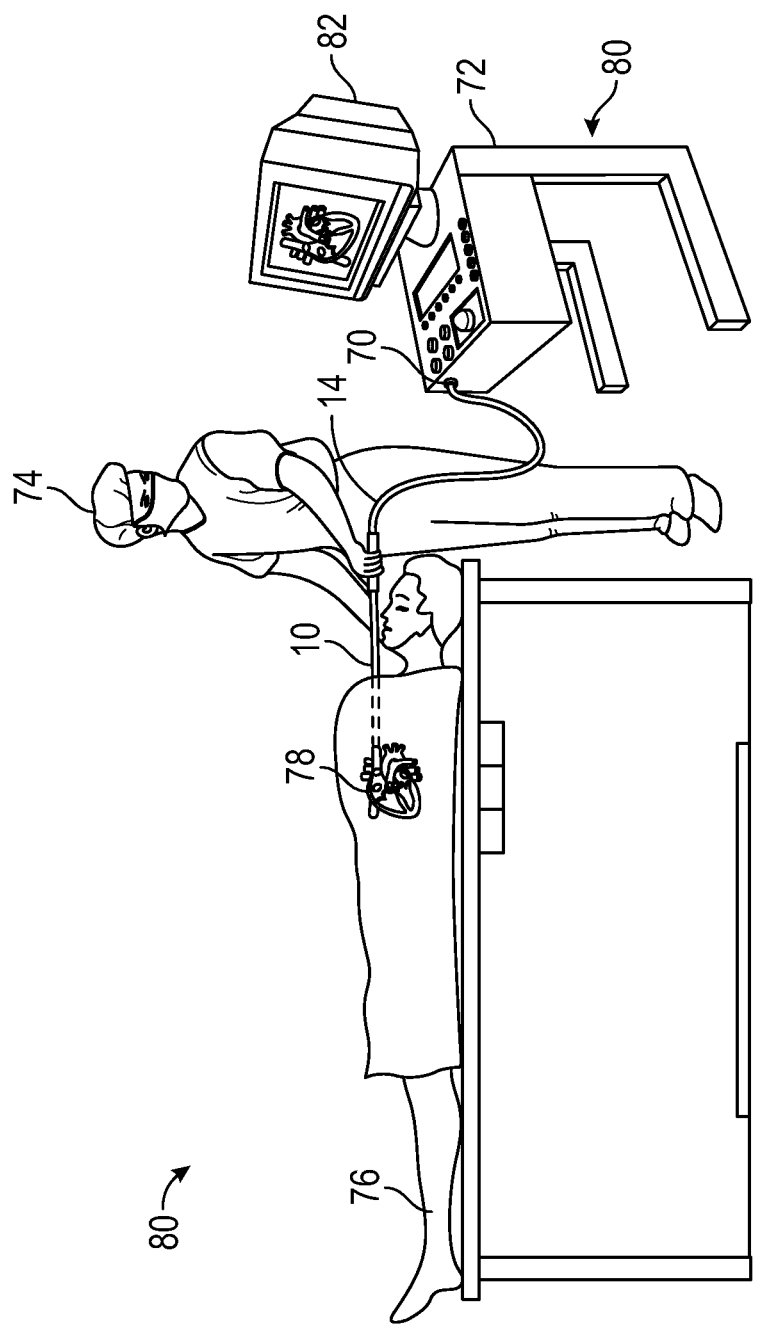
FIG. 7 is a schematic view of an ablation system in accordance with an embodiment of the present invention.

To help illustrate use of the basket-shaped electrode assembly 16, FIG. 7 is a schematic depiction of an invasive medical procedure, according to an embodiment of the present invention. Catheter 10, with the basket-shaped electrode assembly 16 (not shown in this view) at the distal end may have a connector 70 at the proximal end for coupling the wires from their respective electrodes 19 (not shown in this view) to a console 72 for recording and analyzing the signals they detect. An electrophysiologist 74 may insert the catheter 10 into a patient 76 in order to acquire electropotential signals from the heart 78 of the patient. The professional uses the control handle 14 attached to the catheter in order to perform the insertion. Console 72 may include a processing unit 80 which analyzes the received signals, and which may present results of the analysis on a display 82 attached to the console. The results are typically in the form of a map, numerical displays, and/or graphs derived from the signals.

In a further aspect, the processing unit 80 may also receive signals from one or more location sensors 64 provided near a distal end of the catheter 10 adjacent the basket-shaped electrode assembly 16 as schematically indicated in FIG. 1. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 80 to determine the position, (e.g., the location and orientation) of the distal end of catheter 10 within the heart cavity. The electrophysiologist may then view the position of the basket-shaped electrode assembly 16 on an image the patient's heart on the display 82. By way of example, this method of position sensing may be implemented using the CARTO™ system, produced by Biosense Webster Inc. (Diamond Bar, Calif.) and is described in detail in U.S. Pat. Nos. 5,391,199, 6,690,963; 6,484,118; 6,239,724; 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally of the basket-shaped electrode assembly 16. The coordinates of the distal sensor relative to the proximal sensor may be determined and, with other known information pertaining to the curvature of the spines 18 of the basket-shaped electrode assembly 16, used to find the positions of each of the electrodes 19.

Figure 8:
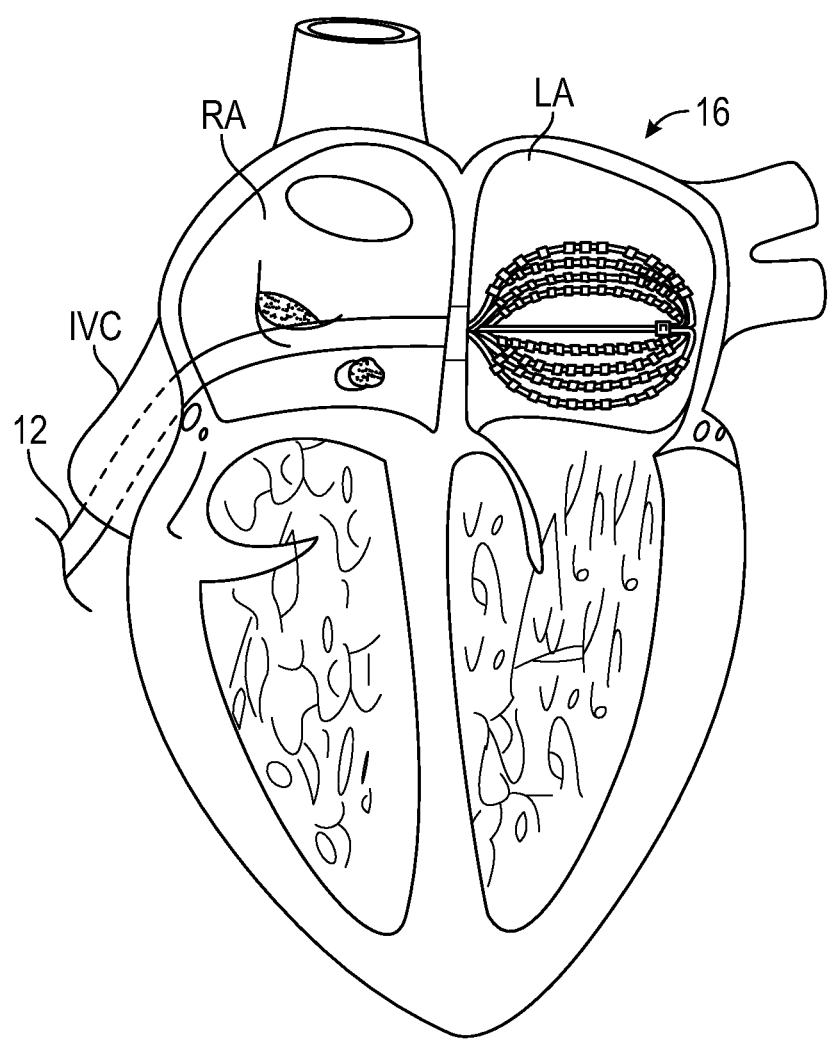
FIG. 8 is a schematic view of the basket-shaped electrode assembly of FIG. 1 deployed in the left atrium.

In one aspect, an electrophysiologist may introduce a guiding sheath, guidewire and dilator into the patient, as is generally known in the art. Examples of suitable guiding sheaths for use in connection with the inventive catheter are the PREFACE™ Braided Guiding Sheath (commercially available from Biosense Webster, Inc., Diamond Bar, Calif.) and the DiRex™ Guiding Sheath (commercially available from BARD, Murray Hill, N.J.). The guidewire is inserted, the dilator is removed, and the catheter is introduced through the guiding sheath whereby the guidewire lumen in the puller permits the catheter to pass over the guidewire. In one exemplary procedure as depicted in FIG. 8, the catheter is first introduced to the right atrium (RA) via the inferior vena cava (IVC), where it passes through the septum (S) in order to reach the left atrium (LA).

As will be appreciated, the guiding sheath covers the spines 18 of the basket-shaped electrode assembly 16 in a collapsed position so that the entire catheter can be passed through the patient's vasculature to the desired location. The puller 22 may be positioned distally of the catheter body to allow the spines of the assembly to be flattened while the assembly is passed through the guiding sheath. Once the distal end of the catheter reaches the desired location, e.g., the left atrium, the guiding sheath is withdrawn to expose the basket-shaped electrode assembly 16. The puller 22 is drawn proximally through its first range of travel or otherwise manipulated so that the spines 18 flex outwardly between the distal and proximal junctions. With the basket-shaped electrode assembly 16 radially expanded, the ring electrodes 19 contact atrial tissue. As recognized by one skilled in the art, the basket-shaped electrode assembly 16 may be fully or partially expanded into the first deployed expanded configuration as shown in FIG. 8. Further, aspects of the configuration of basket-shaped electrode assembly 16 may be tailored to more closely conform to the area in which it is deployed as discussed above.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising: an elongated body, having a proximal end and a distal end; an electrode assembly mounted at the distal end of the elongated body, the electrode assembly comprising a plurality of spines forming a basket-shaped electrode assembly; a first inner irrigation lumen disposed within the elongated body and extending from the proximal end to the distal end; a second inner lumen disposed adjacent to the first inner lumen and extending from the proximal end to the distal end, the second inner lumen being configured to house a pull-wire disposed longitudinally therein; a spine collar, the spine collar having a length extending from the proximal end to the distal end of the elongated body and a plurality of outer lumens extending along the full length of the spine collar, the first inner lumen and second inner lumen being disposed within the spine collar; and a seal, the seal composed of a thin sheet of material, the seal having a first opening directly aligned with the first inner lumen and a second opening directly aligned with the second inner lumen configured to provide a friction fit seal around an outer surface of the pull-wire, wherein a proximal surface of the seal is fixedly attached to a distal end of the spine collar.

2. The catheter of claim 1, wherein each of the plurality of spines is attached to and in communication with one of the plurality of outer lumens.

3. The catheter of claim 2, wherein each spine comprises at least one ring electrode.

4. The catheter of claim 3, wherein the at least one ring electrode has at least one wire in electrical communication with a controller.

5. The catheter of claim 4, wherein the at least one wire is disposed within a corresponding outer lumen of the plurality of outer lumens.

6. The catheter of claim 1, wherein the seal is composed of silicon.

7. The catheter of claim 6, wherein the first opening and the second opening are laser cut.

8. The catheter of claim 1, further comprising at least one sensor, the at least one sensor operably connected to the electrode assembly and to a controller.

9. A method for the ablation of a portion of tissue of a patient by an operator comprising: inserting a catheter into the patient, wherein the catheter comprises: an elongated body, having a proximal end and a distal end; an electrode assembly mounted at the distal end of the elongated body, the electrode assembly comprising a plurality of spines forming a basket-shaped electrode assembly; a first inner irrigation lumen disposed within the elongated body and extending from the proximal end to the distal end; a second inner lumen disposed adjacent to the first inner lumen and extending from the proximal end to the distal end, the second inner lumen being configured to house a pull-wire disposed longitudinally therein; a spine collar, the spine collar having a length extending from the proximal end to the distal end of the elongated body and a plurality of outer lumens extending along the full length of the spine collar, the first inner lumen and second inner lumen being disposed within the spine collar; and a seal, the seal composed of a thin sheet of material, the seal having a first opening directly aligned with the first inner lumen and a second opening directly aligned with the second inner lumen configured to provide a friction fit seal around an outer surface of the pull-wire, wherein a proximal surface of the seal is fixedly attached to a distal end of the spine collar; connecting the catheter to a system controller capable of receiving signals from a plurality of sensors and delivering power to the electrode assembly; and controlling the power to the electrode assembly to ablate the portion of tissue.

10. The method of claim 9, wherein controlling the power to the electrode assembly to ablate the portion of tissue is based at least in part on measurements from the plurality of sensors.

11. The method of claim 9, further comprising digitizing signals received from the sensors before transmitting them along the elongated body.

12. The method of claim 9, wherein each of the plurality of spines is attached to and in communication with one of the plurality of outer lumens.

13. The method of claim 12, wherein each spine comprises at least one ring electrode.

14. The method of claim 13, wherein the at least one ring electrode has at least one wire in electrical communication with the system controller.

15. The method of claim 14, wherein the at least one wire is disposed within a corresponding outer lumen of the plurality of outer lumens.

16. The method of claim 9, wherein the seal is composed of silicon.

17. The method of claim 16, wherein the first opening and the second opening are laser cut.

* * * * *